(12) United States Patent
Jonckx et al.

(10) Patent No.: US 9,089,552 B2
(45) Date of Patent: Jul. 28, 2015

(54) IMPROVING TRABECULECTOMY OUTCOME BY ADMINISTERING AN ANTI-PLACENTAL GROWTH FACTOR ANTIBODY

(71) Applicant: ThromboGenics NV, Heverlee/Leuven (BE)

(72) Inventors: Bart Jonckx, Oud-Heverlee (BE); Tine Van Bergen, Hoogstraten (BE); Ingeborg Stalmans, Knokke (BE)

(73) Assignee: ThromboGenics NV, Heverlee/Leuven (BE)

( * ) Notice: Subject to any disclaimer, the term of this patent is extended or adjusted under 35 U.S.C. 154(b) by 0 days.

(21) Appl. No.: 13/800,912

(22) Filed: Mar. 13, 2013

(65) Prior Publication Data

US 2013/0195889 A1   Aug. 1, 2013

Related U.S. Application Data

(63) Continuation-in-part of application No. PCT/EP2012/074195, filed on Dec. 3, 2012.

(60) Provisional application No. 61/565,676, filed on Dec. 1, 2011.

(51) Int. Cl.
| | |
|---|---|
| C07K 16/22 | (2006.01) |
| A61K 39/395 | (2006.01) |
| A61P 27/02 | (2006.01) |
| A61K 9/00 | (2006.01) |
| A61K 45/06 | (2006.01) |
| C07K 14/475 | (2006.01) |
| A61K 39/00 | (2006.01) |

(52) U.S. Cl.
CPC ........... *A61K 39/3955* (2013.01); *A61K 9/0048* (2013.01); *A61K 45/06* (2013.01); *C07K 16/22* (2013.01); *A61K 2039/505* (2013.01); *A61K 2039/54* (2013.01); *C07K 14/475* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 5,304,118 A | 4/1994 | Trese et al. | |
| 5,545,806 A | 8/1996 | Lonberg et al. | |
| 5,851,999 A | 12/1998 | Ullrich et al. | |
| 5,919,899 A | 7/1999 | Persico et al. | |
| 6,365,157 B2 | 4/2002 | Rockwell et al. | |
| 6,369,204 B1 | 4/2002 | Kim et al. | |
| 6,455,283 B1 | 9/2002 | Ferrara et al. | |
| 6,733,755 B2 | 5/2004 | Tchistiakova et al. | |
| 6,986,890 B1 | 1/2006 | Shitara et al. | |
| 7,357,929 B2 | 4/2008 | Carmeliet et al. | |
| 7,482,004 B2 | 1/2009 | Carmeliet et al. | |
| 7,642,239 B2 | 1/2010 | Taylor et al. | |
| 7,867,490 B2 | 1/2011 | Carmeliet et al. | |
| 7,875,704 B2 | 1/2011 | Stassen et al. | |
| 2002/0009750 A1 | 1/2002 | Rockwell et al. | |
| 2003/0180286 A1 | 9/2003 | Carmeliet et al. | |
| 2005/0175609 A1 | 8/2005 | Carmeliet et al. | |
| 2008/0193455 A1 | 8/2008 | Stassen et al. | |
| 2009/0074765 A1 | 3/2009 | Carmeliet et al. | |
| 2009/0111974 A1 | 4/2009 | Carmeliet et al. | |
| 2009/0162354 A1 | 6/2009 | Carmeliet et al. | |
| 2009/0238826 A1 | 9/2009 | Carmeliet et al. | |
| 2012/0114630 A1* | 5/2012 | Zwaal | 424/94.64 |
| 2012/0189609 A1* | 7/2012 | Stassen et al. | 424/94.64 |

FOREIGN PATENT DOCUMENTS

| | | |
|---|---|---|
| EP | 1 297 016 | 3/2006 |
| EP | 1 517 703 | 3/2007 |
| EP | 1 869 085 | 3/2012 |
| EP | 1 904 095 | 5/2013 |
| JP | 2001-086982 | 4/2001 |
| WO | WO 84/03564 | 9/1984 |
| WO | WO 96/30046 | 10/1996 |
| WO | WO 97/15330 | 5/1997 |
| WO | WO 98/13071 | 4/1998 |
| WO | WO 99/24056 | 5/1999 |
| WO | WO 99/60846 | 12/1999 |
| WO | WO 01/04269 | 1/2001 |
| WO | WO 01/85796 | 11/2001 |
| WO | WO 03/000183 | 1/2003 |
| WO | WO 03/063904 | 8/2003 |
| WO | WO 03/103581 | 12/2003 |
| WO | WO 2004/002524 | 1/2004 |
| WO | WO 2004/052228 | 6/2004 |
| WO | WO 2005/016455 | 2/2005 |
| WO | WO 2006/099698 | 9/2006 |
| WO | WO 2007/003609 | 1/2007 |
| WO | WO 2007/047609 | 4/2007 |

(Continued)

OTHER PUBLICATIONS

Van Bergen et al. Inhibition of placenta growth factor improves surgical outcome of glaucoma surgery. Acta Ophthalmologica 90(Suppl s249): p. 0, Sep. 2012.*
Van Bergen et al. Inhibition of placenta growth factor improves surgical outcome of glaucoma surgery. J Cell Mol Med 17(12): 1632-1643, 2013.*
Van Bergen et al. Improving patient outcomes following glaucoma surgery: state of the art and future perspectives. Clin Ophthalmology 8: 857-867, 2014.*
Addicks et al., "Histologic characteristics of filtering blebs in glaucomatous eyes," *Arch Opthalmol.*, 101:795-798 (1983).
Ahmed et al., "Regulation of placental vascular endothelial growth factor (VEGF) and placenta growth factor (PlGF) and soluble Flt-1 by oxygen—a review," *Placenta*, 21 Suppl A:S16-S24 (2000).
Attwood, TK, "Genomics. The Babel of bioinformatics," *Science*, 290:471-473 (2000).
Bais et al., "PlGF blockade does not inhibit angiogenesis during primary tumor growth," *Cell*, 141:166-177 (2010).

(Continued)

*Primary Examiner* — Bridget E Bunner
(74) *Attorney, Agent, or Firm* — Fish & Richardson P.C.

(57) ABSTRACT

The current invention relates to the improvement of trabeculectomy surgery. The improvement more specifically resides in an extended lifetime of the sclera-corneal drainage channel created by trabeculectomy surgery. The improvement is obtained by post-surgical administration of an anti-PlGF antibody or fragment thereof.

19 Claims, 9 Drawing Sheets

(56) References Cited

FOREIGN PATENT DOCUMENTS

Figure 1:
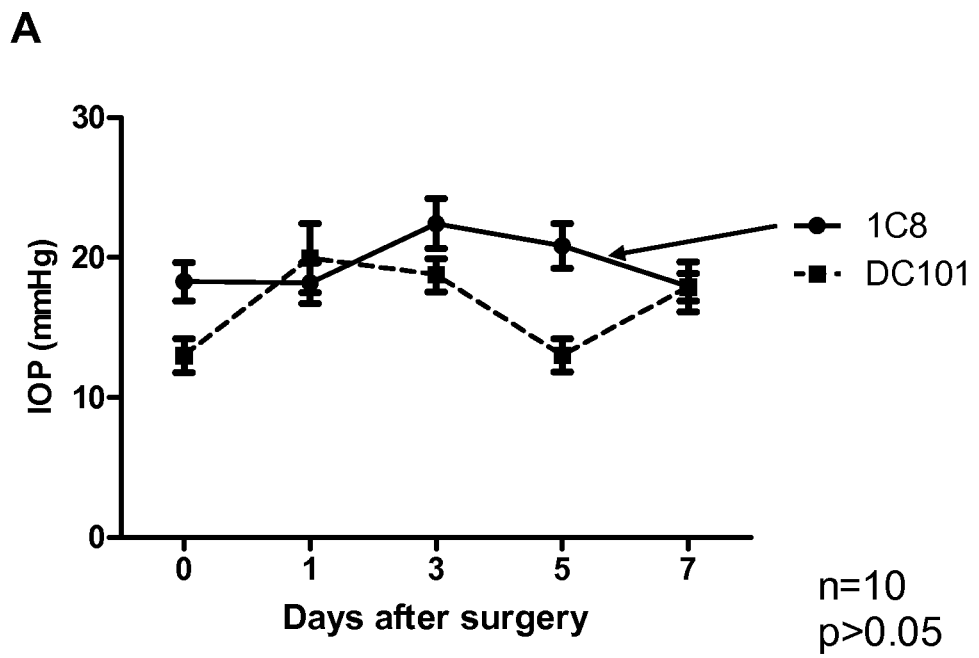
Figure 1:
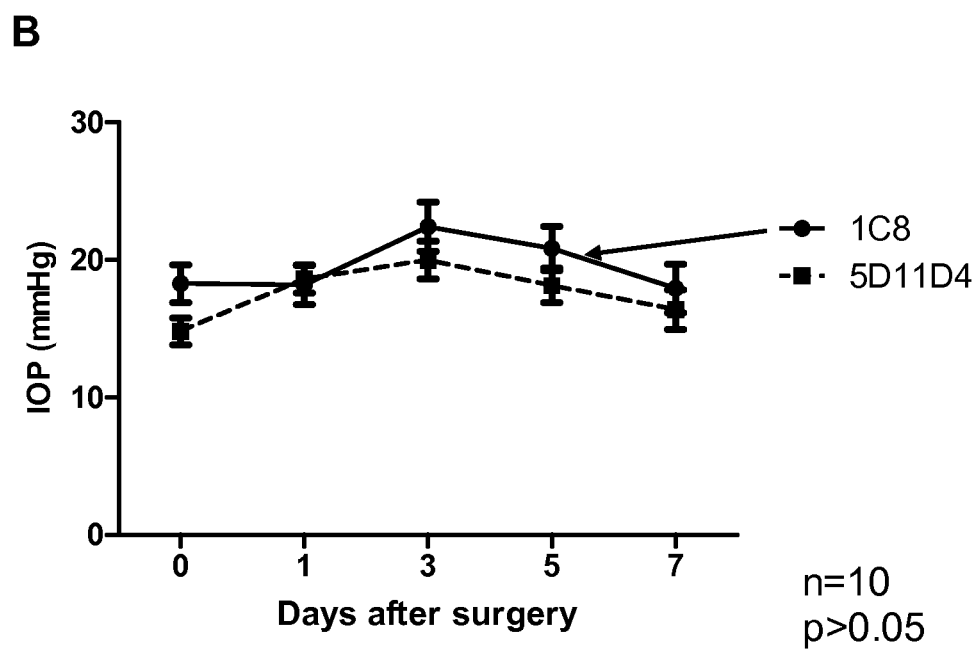

| WO | WO 2009/067407 | | 5/2009 |
|---|---|---|---|
| WO | WO 2009/073457 | | 6/2009 |
| WO | WO 2010/037864 | | 4/2010 |
| WO | WO 2010/097800 | | 9/2010 |
| WO | WO-2011004001 | A1 * | 1/2011 |
| WO | WO 2011/023805 | | 3/2011 |

OTHER PUBLICATIONS

Barillari et al., "The basic residues of placenta growth factor type 2 retrieve sequestered angiogenic factors into a soluble form: implications for tumor angiogenesis," *Am J Pathol.*, 152:1161-1166 (1998).
Bernatchez et al., "Vascular endothelial growth factor effect on endothelial cell proliferation, migration, and platelet-activating factor synthesis is Flk-1-dependent," *J Biol Chem.*, 274:31047-31054 (1999).
Bicknell et al., In: Tumor Angiogenesis, chapter 2, pp. 1-3 and 5-18 (1997).
Bottomley et al., "Placenta growth factor (P1GF) induces vascular endothelial growth factor (VEGF) secretion from mononuclear cells and is co-expressed with VEGF in synovial fluid," *Clin Exp Immunol.*, 119:182-188 (2000).
Boulton et al., "Placental growth factor localisation in diabetic retinas and preretinal membranes," *Invest Ophthalmol. Vis. Sci.*, 38:S965 (1997).
Brenchley, P.E.C., "Angiogenesis in inflammatory joint disease: a target for therapeutic intervention," *Clin Exp Immunol.*, 121:426-429 (2000).
Brenchley, P. "Antagonising the expression of VEGF in pathological angiogenesis," *Exp. Opin. Ther. Patents*, 8:1695-1706 (1998).
Burr et al., "Medical versus surgical interventions for open angle glaucoma," *Cochrane Database Syst Rev.*, 18(2):CD004399 (2005).
Carmeliet, P., "Molecular mechanisms of normal and pathologic angiogenesis: insights and therapeutic concepts from transgenic cells," Journal of Vascular Research, 37(suppl 1):79 (2000).
Carmeliet et al., "Molecular analysis of blood vessel formation and disease," *Am J Physiol.*, 273:H2091-H104 (1997).
Carmeliet et al., "Role of vascular endothelial growth factor and vascular endothelial growth factor receptors in vascular development," *Curr Top Microbiol Immunol.*, 237:133-158 (1999).
Carmeliet, P., "Basic Concepts of (Myocardial) Angiogenesis: Role of Vascular Endothelial Growth Factor and Angiopoietin," *Curr Interv Cardiol Rep.*, 1:322-335 (1999).
Carmeliet et al., "Transgenic mouse models in angiogenesis and cardiovascular disease," *J Pathol.*, 190:387-405 (2000).
Carmeliet, P., "Mechanisms of angiogenesis and arteriogenesis," *Nat Med.*, 6:389-395 (2000).
Carmeliet et al., "Synergism between vascular endothelial growth factor and placental growth factor contributes to angiogenesis and plasma extravasation in pathological conditions," *Nat Med.*, 7:575-583 (2001).
Carmeliet, P., "Gene targeting and gene transfer to unravel the molecular basis of the formation and disorders of blood vessels," *Verh K Acad Geneesk Belg.*, 62:31-68 (2000).
Casset et al., 2003, "A peptide mimetic of an anti-CD4 monoclonal antibody by rational design," *Biochem Biophys Res Commun.*, 307:198-205 (2003).
CAT-152 0102 Trabeculectomy Study Group, "A phase III study of subconjunctival human anti-transforming growth factor β2 monoclonal antibody (CAT-152) to prevent scarring after first-time trabeculectomy," *Ophthalmology*, 114:1822-1830 (2007 by the American Academy of Ophthalmology).
Chen et al., "Selection and analysis of an optimized anti-VEGF antibody: crystal structure of an affinity-matured Fab in complex with antigen," *J Mol Biol.*, 293:865-881 (1999).
Christinger et al., "The crystal structure of placental growth factor in complex with domain 2 of vascular endothelial growth factor receptor-1," *J Biol Chem.*, 279:10382-10388 (2004).
Collaborative Normal-Tension Glaucoma Study Group, "Comparison of glaucomatous progression between untreated patients with normal-tension glaucoma and patients with therapeutically reduced intraocular pressures," *Am J Opthalmol.*, 126: 487-497 (1998).
Colucciello, M., "Diabetic retinopathy. Control of systemic factors preserves vision," *Postgrad Med.*, 116:57-64 (2004).
Cordeiro et al., "Novel antisense oligonucleotides targeting TGF-beta inhibit in vivo scarring and improve surgical outcome," *Gene Ther.*, 10:59-71 (2003).
Cortes et al., "Investigational strategies in chronic myelogenous leukemia," *Hematol Oncol Clin North Am.*, 18: 619-639 (2004).
Declerck et al., "Generation of monoclonal antibodies against autologous proteins in gene-inactivated mice," *J Biol Chem.*, 270:8397-8400 (1995).
dePascalis et al., "Grafting of "abbreviated" complementarity-determining regions containing specificity-determining residues essential for ligand contact to engineer a less immunogenic humanized monoclonal antibody," *J. Immunol.*, 169:3076-3084 (2002).
Dias et al., "Inhibition of both paracrine and autocrine VEGF/VEGFR-2 signaling pathways is essential to induce long-term remission of xenotransplanted human leukemias," *Proc Natl Acad Sci U S A.*, 98:10857-10862 (2001).
Donnini et al.,, "Expression and localization of placenta growth factor and P1GF receptors in human meningiomas," *J Pathol.*, 189:66-71 (1999).
Ferrara et al., "Clinical applications of angiogenic growth factors and their inhibitors," *Nat Med.*, 5:1359-1364 (1999).
Fidler et al., "Cancer, Principles and Practice of Oncology," 6$^{th}$ Edition, chapter 9, 137-147 (Lippincott Williams & Wilkins) (2001).
Fischer et al., "Anti-PlGF inhibits growth of VEGF(R)-inhibitor-resistant tumors without affecting healthy vessels," *Cell*, 131:463-475 (2007).
Fischer et al., "Anti-PlGF inhibits growth of VEGF(R)-inhibitor-resistant tumors without affecting healthy vessels," *Cell*, 131:463-475 (2007) (supplemental data).
Folkman et al., "Seminars in Medicine of the Beth Israel Hospital, Boston. Clinical applications of research on angiogenesis," *N Engl J Med.*, 333:1757-1763 (1995).
Fragoso et al., "VEGRF-1 (FLT-1) activation modulates acute lymphoblastic leukemia localization and survival within the bone marrow, determining the onset of extramedullary disease," *Blood*, 107:1608-1616 (2006).
GenBank: AF260738.1, "*Homo sapiens* platelet-derived growth factor C (PDGFC) mRNA, complete cds," (2001).
Gilbertson et al., "Platelet-derived growth Factor C (PDGF-C), a novel growth factor that binds to PDGF alpha and beta receptor," *J Biol Chem.*, 276:27406-27414 (2001).
Gillies et al., "Cytokines, fibrosis and the failure of glaucoma filtration surgery," *Aust NZ J Ophthalmol.*, 19:299-304 (1991).
Greenfield et al., "Late-onset bleb leaks after glaucoma filtering surgery," *Arch Ophthalmol.*, 116:443-447 (1998).
Griffioen et al., "Angiogenesis: potentials for pharmacologic intervention in the treatment of cancer, cardiovascular diseases, and chronic inflammation," *Pharmacol Rev.*, 52:237-268 (2000).
Guidi et al., "Expression of vascular permeability factor (vascular endothelial growth factor) and its receptors in endometrial carcinoma," *Cancer*, 78:454-460 (1996).
Gura, T., "Systems for identifying new drugs are often faulty," *Science*, 278:1041-1042 (1997).
Hansma et al., "Recombinant human endostatin administered as a 28-day continuous intravenous infusion, followed by daily subcutaneous injections: a phase I and pharmacokinetic study in patients with advanced cancer," *Ann Oncol.*, 16:1695-1701 (2005).
Hazelton et al., "Vascular endothelial growth factor in ovarian cancer," *Curr Oncol Rep.*, 1:59-63 (1999).
Hitchings et al., "Clinico pathological correlation in eyes with failed fistulizing surgery," *Trans Ophthalmol Soc UK*, 103:84-88 (1983).
Hitchings, R., "Initial treatment for open-angle glaucoma- medical, laser, or surgical? Surgery is the treatment of choice for open-angle glaucoma," *Arch Ophthalmol.*, 116:241-242 (1998).
Holm et al., "Functional mapping and single chain construction of the anti-cytokeratin 8 monoclonal antibody TS1," *Mol. Immunol.*, 44:1075-1084 (2007).

(56) References Cited

OTHER PUBLICATIONS

Ikai et al., "Placenta growth factor stimulates the growth of Philadelphia chromosome positive acute lymphoblastic leukemia cells by both autocrine and paracrine pathways," *Eur. J. Haematol.*, 75:273-279 (2005).

Inoue et al., "Mechanism of mustard oil-induced skin inflammation in mice," *Eur J Pharmacol.*, 333:231-240 (1997).

Interlocutory Decision of Opposition Division in Opposition Strawman Limited in European Patent EP1297016B1, dated Mar. 27, 2009.

Iyer et al., "The crystal structure of human placenta growth factor-1 (P1GF-1), an angiogenic protein, at 2.0 A resolution," *J. Biol. Chem.*, 276:12153-12161 (2001).

Jain et al., "alpha PIGF: a new kid on the antiangiogenesis block," *Cell*, 131:443-445 (2007).

Jampel et al., "Cellular proliferation after experimental glaucoma filtration surgery," *Arch Ophthalmol.*, 106:89-94 (1988).

Johnstone & Thorpe, In: Immunochemistry in practice, *Blackwell Scientific Publications*, Oxford, p. 30 (1987).

Kanno et al., "Roles of two VEGF receptors, Flt-1 and KDR, in the signal transduction of VEGF effects in human vascular endothelial cells," *Oncogene*, 19:2138-2146 (2000).

Katoh et al., "Expression of vascular endothelial growth factor (VEGF) in human thyroid neoplasms," *Hum Pathol.*, 30(8):891-897 (1999).

Katz et al., "Mitomycin C versus 5-fluorouracil in high-risk glaucoma filtering surgery. Extended follow-up," *Ophthalmology*, 102:1263-1269 (1995).

Khaliq et al., "Increased expression of placenta growth factor in proliferative diabetic retinopathy," *Lab Invest.*, 78, 109-116 (1998).

King et al., "Frequency of bleb manipulations after trabeculectomy surgery," *Br J Ophthalmol.*, 91:873-877(2007).

Kohler & Mistein, "Continuous cultures of fused cells secreting antibody of predefined specificity," *Nature*, 256:495-497; (1975); reprinted in *J. Immunol.*, 174:2453-2455 (2005).

Lama et al., "Antifibrotics and wound healing in glaucoma surgery," *Surv Ophthalmol.*, 48:314-346 (2003).

Laurin et al., "Paget disease of bone: mapping of two loci at 5q35-qter and 5q31," *Am. J. Hum. Genet.*, 69:528-543 (2001).

Lee et al., "Treatment of failing glaucoma filtering cystic blebs with tissue plasminogen activator (tPA)," *J Ocul Pharmacol Ther.*, 11:227-232 (1995).

Li et al, "Inhibition of vascular endothelial growth factor reduces scar formation after glaucoma filtration surgery," *Invest Ophthalmol Vis Sci.*, 50:5217-5225 (2009).

Li et al., "Role of vascular endothelial growth factor and placental growth factor in glaucoma and scar formation after glaucoma filtration surgery," Free papers glaucoma: microbiology and bloodflow and IOP (2006).

Loges et al., "Evaluation of the role of PLGF and the therapeutic potential of anti-PLGF in BCR/ABL+ leukemia," *Blood*, 112: Abstract 1094 (2008).

Lou, K.-J., "Markers for interferon responsiveness in MS," *SciBX*, 3(16):5-7 (2010).

Luttun et al., "Loss of placental growth factor protects mice against vascular permeability in pathological conditions," *Biochem Biophys Res Commun.*, 295:428-434 (2002).

Luttun et al., "Genetic dissection of tumor angiogenesis: are PLGF and VEGFR-1 novel anti-cancer targets?," *Biochim Biophys Acta*, 1654:79-94 (2004).

MacCallum et al., "Antibody-antigen interactions: contact analysis and binding site topography," *J Mol. Biol.*, 262:732-745 (1996).

Maglione et al., "Isolation of a human placenta cDNA coding for a protein related to the vascular permeability factor," *Proc. Natl. Acad. Sci. U. S. A.*, 88:9267-9271 (1991).

Maglione et al., "Two alternative mRNAs coding for the angiogenic factor, placenta growth factor (P1GF), are transcribed from a single gene of chromosome 14," *Oncogene*, 8:925-931 (1993).

Maragoudakis, M. Angiogenesis: From the Molecular to Integrative Pharmacology, *Advances in Experimental Medicine and Biology, Proceedings of the 5th Biannual International Meeting on Angiogenesis*, 476:1-4 (held on Jul. 1-7, 1999) (Published in 2000 by Kluwer Academic/Plenum Publishers).

May et al., "Peptide epitopes from the Wilms' tumor 1 oncoprotein stimulate CD4+ and CD8+ T cells that recognize and kill human malignant mesothelioma tumor cells," *Clin. Cancer Res.*, 13:4547-4555 (2007).

Mayr-Wohlfart et al., "Vascular endothelial growth factor stimulates chemotactic migration of primary human osteoblasts," *Bone*, 30:472-477 (2002).

Migdal et al., "Neuropilin-1 is a placenta growth factor-2 receptor," *J Biol Chem.*, 273:22272-22278 (1998).

Miller, KD., "Issues and challenges for antiangiogenic therapies," *Breast Cancer Res Treat.*, 75:S45-S50 (2002).

Mitamura et al., "Placenta growth factor and vascular endothelial growth factor in the vitreous of patients with proliferative vitreoretinopathy," *Clin. Experiment. Ophthalmol.*, 33:226-227 (2005).

MSNBC News Services, Online News "Mixed results on new cancer drugs," (Nov. 9, 2000).

Mueller et al., "Expression of tissue factor by melanoma cells promotes efficient hematogenous metastasis," *Proc. Natl. Acad. Sci. U. S.A.*, 89:11832-11836 (1992).

Nicol et al., "Vascular endothelial growth factor expression is increased in renal cell carcinoma," *J Urol.*, 157:1482-1486 (1997).

Niida et al., "Vascular endothelial growth factor can substitute for macrophage colony-stimulating factor in the support of osteoclastic bone resorption," *J. Exp. Med.*, 190:293-298 (1999).

Nomura et al., "Placenta growth factor (PLGF) mRNA expression in brain tumors," *J Neurooncol.*, 40:123-130 (1998).

Notice of Opposition Strawman Limited in European Patent EP1297016B1, dated Dec. 20, 2006.

Oliver et al., "Suppression of collagen-induced arthritis by an angiogenesis inhibitor, AGM-1470, in combination with cyclosporin: reduction of vascular endothelial growth factor (VEGF)," *Cell Immunol.*, 166:196-206 (1995).

Paleolog et al., "Angiogenesis in arthritis: role in disease pathogenesis and as a potential therapeutic target," *Angiogenesis*, 2:295-307 (1998).

Paques et al., "Growth factors and diabetic retinopathy," *Diabetes Metab.*, 23:125-130 (1997).

Park et al., "Placenta growth factor. Potentiation of vascular endothelial growth factor bioactivity, in vitro and in vivo, and high affinity binding to Flt-1 but not to Flk-1/KDR," *J Biol Chem.*, 269:25646:25654 (1994).

Parry et al., "Bioactivity of anti-angiogenic ribozymes targeting Flt-1 and KDR mRNA," *Nucleic Acids Res.*, 27: 2569-2577 (1999).

Puccetti et al., "BCR-ABL mediates arsenic trioxide-induced apoptosis independently of its aberrant kinase activity," *Cancer Res.*, 60:3409-3413 (2000).

Queen et al., "A humanized antibody that binds to the interleukin 2 receptor," *Proc Natl Acad Sci USA*, 86:10029-10033 (1989).

Quigley, HA., "Number of people with glaucoma worldwide," *Br J Ophthalmol.*, 80:389-393 (1996).

R&D Systems, "Biotinylated Anti-mouse PLGF-2 Antibody," Catalog No. BAF465 (Jan. 21, 1999).

R&D Systems, "Monoclonal anti-mouse PLGF-2 Antibody," Catalog No. MAB465 (Oct. 18, 1999).

R&D Systems, "Monoclonal anti-human PLGF Antibody," Catalog No. MAB264 (Jun. 26, 2001).

Robinson et al., "Nonvascular role for VEGF: VEGFR-1, 2 activity is critical for neural retinal development.," *FASEB J.*, 15:1215-1217 (2001).

Rudikoff et al., "Single amino acid substitution altering antigen-binding specificity," *Proc. Natl. Acad. Sci. USA*, 79:1979-1983 (1982).

Ryan et al., "Preclinical safety evaluation of rhuMAbVEGF, an antiangiogenic humanized monoclonal antibody," *Toxicol Pathol.*, 27:78-86 (1999).

Shirasaki et al., "Vascular endothelial growth factor plays an important role in chronic myologenous leukemia: relationship to disease-progression," *Haematologica* 93(Supp 1):538-539 (2008).

(56) References Cited

OTHER PUBLICATIONS

Skolnick et al., "From genes to protein structure and function: novel applications of computational approaches in the genomic era," *Trends Biotechnol.*, 18:34-39 (2000).

Skuta et al., "Wound healing in glaucoma filtering surgery," *Surv Ophthalmol.*, 32:149-170 (1987).

Stalmans et al., "Enzymatic vitreolysis with ocriplasmin for vitreomacular traction and macular holes," *N Engl J Med.*, 367:606-615 (2012).

Statement of Grounds of Appeal of Opponent Strawman Limited in European Patent EP1297016B1, dated Aug. 6, 2009.

Takahashi et al., "Markedly increased amounts of messenger RNAs for vascular endothelial growth factor and placenta growth factor in renal cell carcinoma associated with angiogenesis," *Cancer Res.*, 54:4233-4237 (1994).

Vajdos et al., "Comprehensive functional maps of the antigen-binding site of an anti-ErbB2 antibody obtained with shotgun scanning mutagenesis," *J. Mol. Biol.*, 320: 415-428 (2002).

Van Bergen et al., "Role of placental growth factor (PLGF) in wound healing after glaucoma filtration surgery," *Bull Soc Belge Ophtalmol.*, 317:65-66 (2011).

Van Bergen et al., "The role of different VEGF isoforms in scar formation after glaucoma filtration surgery," *Exp Eye Res.*, 93:689-699 (2011).

Van de Veire et al., Further pharmacological and genetic evidence for the efficacy of P1GF inhibition in cancer and eye disease, *Cell*, 141:178-190 (2010).

Verstovsek et al., "Clinical relevance of VEGF receptors 1 and 2 in patients with chronic myelogenous leukemia," *Leuk. Res.*, 27:661-669 (2003).

Verstovsek et al., "Prognostic significance of cellular vascular endothelial growth factor expression in chronic phase chronic myeloid leukemia," *Blood*, 99:2265-2267 (2002).

Viglietto et al., "Upregulation of vascular endothelial growth factor (VEGF) and downregulation of placenta growth factor (P1GF) associated with malignancy in human thyroid tumors and cell lines," *Oncogene*, 11:1569-1579 (1995).

Viglietto et al., "Neovascularization in human germ cell tumors correlates with a marked increase in the expression of the vascular endothelial growth factor but not the placenta-derived growth factor," *Oncogene*, 13:577-587 (1996).

Weindel et al., "Detection and quantification of vascular endothelial growth factor/vascular permeability factor in brain tumor tissue and cyst fluid: the key to angiogenesis?," *Neurosurgery*, 35:439-449 (1994).

Wu et al., "Humanization of a murine monoclonal antibody by simultaneous optimization of framework and CDR residues," *J. Mol. Biol.*, 294:151-162 (1999).

Yonekura et al., "Placenta growth factor and vascular endothelial growth factor B and C expression in microvascular endothelial cells and pericytes. Implication in autocrine and paracrine regulation of angiogenesis," *J Biol Chem.*, 274:35172-35178 (1999).

Ziche et al., "Placenta growth factor-1 is chemotactic, mitogenic, and angiogenic," *Lab Invest.*, 76:517-531 (1997).

\* cited by examiner

IMPROVING TRABECULECTOMY OUTCOME BY ADMINISTERING AN ANTI-PLACENTAL GROWTH FACTOR ANTIBODY

CROSS REFERENCE TO RELATED APPLICATIONS

This application is a continuation-in-part of PCT application no. PCT/EP2012/074195, filed Dec. 3, 2012, which claims benefit of U.S. application No. 61/565,676, filed Dec. 1, 2011. The disclosure of the prior applications are considered part of and are incorporated by reference in their entirety in the disclosure of this application.

FIELD OF THE INVENTION

The current invention relates to the improvement of trabeculectomy surgery. The improvement more specifically resides in an extended lifetime of the sclera-corneal drainage channel created by trabeculectomy surgery. The improvement is obtained by administration of an antibody, or antigen-binding fragment thereof, binding to placental growth factor (PlGF) and inhibiting PlGF activity.

BACKGROUND OF THE INVENTION

Glaucoma is a multifactorial, neurodegenerative disease and the second most important cause of irreversible blindness (Quigley, 1996, Br J Ophthalmol 80, 389-393). This disease is characterized by progressive retinal ganglion cell apoptosis, resulting in visual field loss. Current treatment of this disease is directed towards the reduction of intraocular pressure (IOP), which is the main risk factor for glaucoma (Collaborative Normal-Tension Glaucoma Study Group, 1998, Am J Opthalmol 126, 487-497).

Of all currently used treatments to lower IOP, glaucoma filtration surgery (trabeculectomy), or shortly filtration surgery, was shown to be the most effective (Burr et al., 2005, Cochrane Database Syst Rev 18(2):CD004399; Hitchings, 1998, Arch Ophthalmol 116, 241-242). A trabeculectomy creates a "controlled" leak of fluid (aqueous humor) from the eye, which percolates under the conjunctiva. During the operation a piece of trabecular meshwork in the drainage angle of the eye is removed, creating an opening. The opening is partially covered with a flap of tissue from the sclera and conjunctiva. A small conjunctival "bleb" (bubble) appears at the junction of the cornea and the sclera (limbus) where this surgically produced valve is made.

In 30% of the cases, however, the constructed channel closes due to excessive scar tissue formation, resulting in surgical failure (Addicks et al., 1983, Arch Ophthalmol 101, 795-798). The 4 important processes contributing to post-operative conjunctival scarring are: clot formation, inflammation, angiogenesis and fibrosis (Lee et al., 1995, J Ocul Pharmacol Ther 11, 227-232; Lama & Fechtner, 2003, Surv Ophthalmol 48, 314-346). Indeed, increased conjunctival infiltration of inflammatory cells and Tenon fibroblasts (Hitchings & Grierson, 1983, Trans Ophthalmol Soc UK 103, 84-88; Skuta & Parrish, 1987, Surv Ophthalmol 32, 149-170), and higher levels of bleb vascularisation (Jampel et al., 1988, Arch Ophthalmol 106, 89-94) are associated with surgical failure. These processes are mediated by various cytokines (e.g. IL-1 and INF-α2b) and growth factors (e.g. PDGF, FGF, TGF-β1 and VEGF (Lama & Fechtner, 2003; Gillies & Su, 1991, Aust NZ J Ophthalmol 19, 299-304)). Peroperative anti-mitotics, such as mitomycin-C and 5-Fluorouracyl can improve surgical outcome (Quigley, 1996; Katz et al., 1995, Ophthalmol 102, 1263-1269). However, these antimetabolites carry a risk of vision-threatening complications such as scleral thinning and infections (Lama & Fechtner, 2003; Hitchings & Grierson, 1983; Skuta & Parrish, 1987; Jampel et al., 1988; Gillies & Su, 1991; Katz et al., 1995; Greenfield et al., 1998, Arch Ophthalmol 116, 443-447). Furthermore, blocking TGF-β seemed promising in animal models (Cordeiro et al., 2003, Gene Ther 10, 59-71), but was not efficient in a clinical study (CAT-152 0102 Trabeculectomy Study Group, Kwah, Grehn, 2007, Ophthalmol 114, 1822-1830). The number of post-trabeculectomy interventions expressed as the incidence of post-surgery "bleb manipulations" was reported to be as high as 78% (King et al., 2007, Br J Ophthalmol 91, 873-877). Therefore, there is still a need for alternative strategies to prevent filtration failure and, thus, to reduce the incidence of bleb manipulations.

Microplasmin is a recombinant protein that dissolves blood clots by degrading fibrin. Recently, microplasmin has been shown to be efficient, well tolerated and safe for intraocular use (WO 2004/052228) and was approved by FDA in October 2012 for treating vitreomacular adhesion (JETREA®; non-proprietary name: ocriplasmin). Results of the phase III clinical trials leading to this approval were published by Stalmans et al. (2012, N Engl J Med 367, 606-615). Plasmin was previously shown to be able to induce PVD as well (e.g. U.S. Pat. No. 5,304,118). The mechanism by which PVD is induced by plasmin or microplasmin is currently not fully understood. Unsupported by any or any conclusive experimental data, WO 2009/073457 and WO 2009/067407 propose subconjunctival plasmin injection for rescuing filtering blebs and the use of matrix metalloproteinase activating proteases for reducing IOP, respectively. WO 2011/023805 provides the evidence that anterior chamber injection of microplasmin was effective in prolonging bleb survival, i.e., the mode of administration of microplasmin in this indication is determining success.

Pegaptanib is a pegylated anti-VEGF aptamer (VEGF=vascular endothelial growth factor), a single strand of nucleic acid (50 kDa). It specifically binds the $VEGF_{165}$ isoform, thereby preventing the binding to the heparin binding domain. Van Bergen et al. 2011 (Exp Eye Res 93, 689-699) showed that single or repeated injection of pegaptanib after glaucoma filtration surgery (in a rabbit model) had marginal effect on bleb area and bleb survival. Bevacizumab is an antibody inhibiting all forms of VEGF-A. Li et al. 2009 (Invest Ophthalmol Vis Sci 50, 5217-5225) disclosed the effect of bevacizumab on glaucoma filtration surgery (in a rabbit model) which was, judging from the reported effect on bleb area, limited.

SUMMARY OF THE INVENTION

The invention relates to an anti-PlGF (placental growth factor) antibody or fragment thereof for improving or enhancing the success rate of trabeculectomy surgery (or glaucoma filtration surgery) of an eye, or for preventing, reducing or retarding the occurrence of filtration failure after trabeculectomy surgery of an eye.

Alternatively, the invention relates to the use of an anti-PlGF antibody or fragment thereof for the manufacture of a medicament for, or in a method of, improving or enhancing the success rate of trabeculectomy surgery (or glaucoma filtration surgery) of an eye, or for/of preventing, reducing or retarding the occurrence of filtration failure after trabeculectomy surgery of an eye.

The anti-PlGF antibody or fragment thereof as described above may be in a pharmaceutically acceptable formulation capable of being administered to an eye. In particular, said pharmaceutically acceptable formulation is compatible with administration into the anterior chamber of an eye, with in-bleb administration, with administration into the vitreous of an eye, with administration into the subconjunctiva of an eye, or with administration as eye drops.

Said treating of filtration failure after trabeculectomy surgery of an eye, or said preventing, reducing or retarding of the occurrence of filtration failure after trabeculectomy surgery of an eye with an anti-PlGF antibody or fragment thereof as described above in particular results from administering to said eye at least a single dose, or, alternatively, multiple doses, of an effective amount of said anti-PlGF antibody or fragment thereof. When multiple doses are administered to an eye, these may be administered with at least 6-hour time intervals, and may individually be administered in the same or different location. Said eye may be contacted further with one or more agents chosen from an agent for controlling the intra-ocular pressure, an anti-inflammatory agent, an antiviral agent, an antibacterial agent, an antiviral agent, an anti-angiogenic agent, an anti-mitotic agent, an antihistamine, an anesthetic, an agent to induce mydriasis and an agent to induce cycloplegia. Said further contacting may be occurring prior to, concurrent with, or after administering the anti-PlGF antibody or fragment thereof.

The anti-PlGF antibody or fragment thereof as described above may be in a pharmaceutically acceptable formulation further comprising one or more of an agent for controlling the intra-ocular pressure, an anti-inflammatory agent, an antiviral agent, an antibacterial agent, an antiviral agent, an anti-angiogenic agent, an anti-mitotic agent, an antihistamine, an anesthetic, an agent to induce mydriasis and an agent to induce cycloplegia.

FIGURE LEGENDS

FIG. 1. FIG. 1A shows result of measurement of the intra-ocular pressure (IOP) in two groups (group size n=10) that had undergone glaucoma filtration surgery (GFS). One group was treated with 1C8, an irrelevant mouse IgG antibody (4.8 mg/ml) and the other group was treated with DC101, an anti-murine VEGF-R2 antibody (6.2 mg/ml). IOPs were measured with a Tonolab (Technop®). Results are represented as mean±SEM. IOP was not found to be significantly different in the 2 groups (p>0.05). FIG. 1B shows in a similar way the result of measurement of in two groups (group size n=10) that had undergone GFS. One group was treated with 1C8, an irrelevant mouse IgG antibody (4.8 mg/ml) and the other group was treated with 5D11D4, an anti-murine PlGF antibody (5.2 mg/ml). IOP was not found to be significantly different in the 2 groups (p>0.05).

Figure 2:
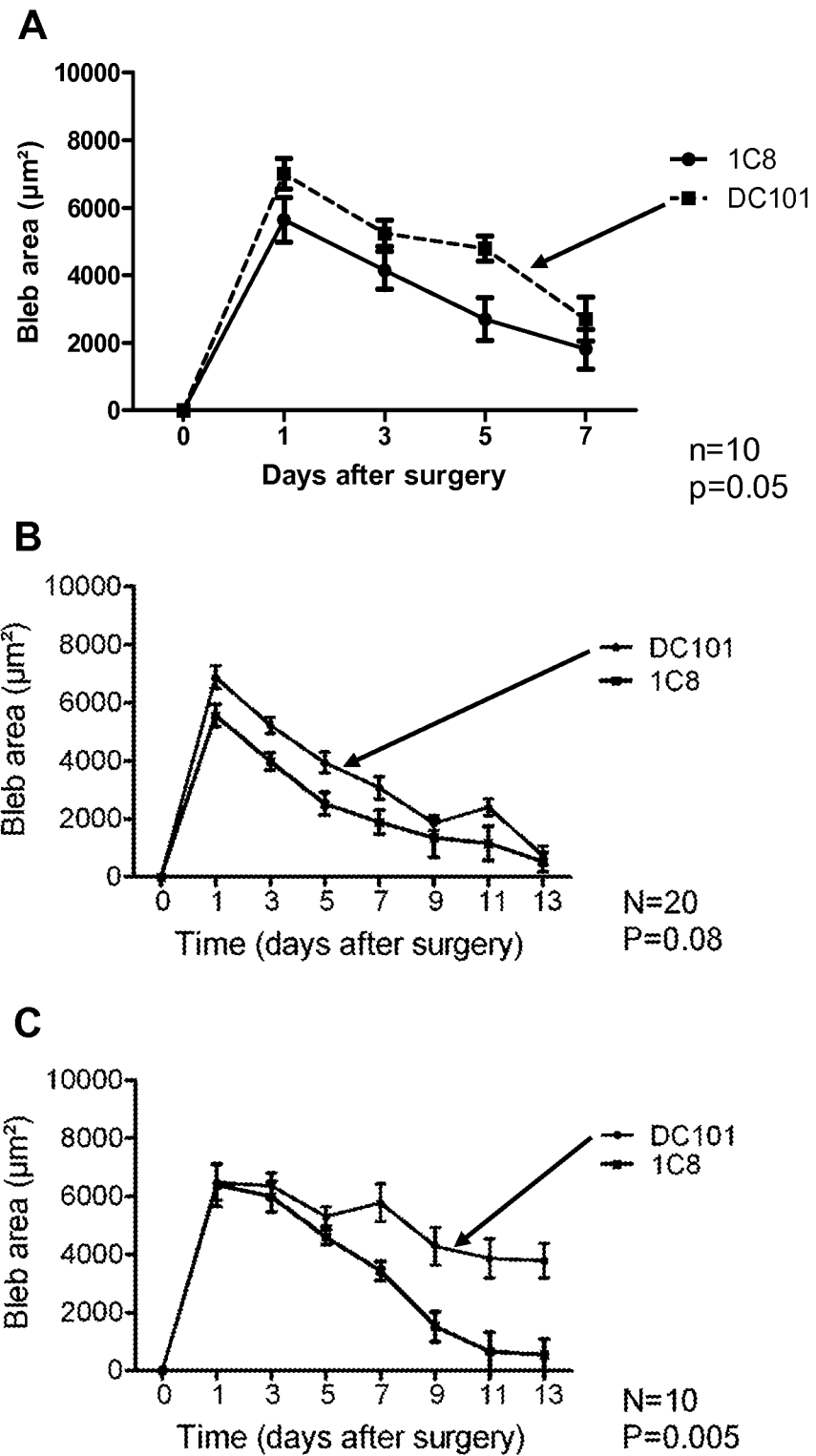

FIG. 2. FIG. 2A shows measurements of bleb area in two groups (group size n=10) that had undergone (GFS). One group was treated with 1C8, an irrelevant mouse IgG antibody (4.8 mg/ml) and the other group was treated with DC101, an anti-murine VEGF-R2 antibody (6.2 mg/ml). Results are represented as mean±SEM. DC101 significantly improved bleb area as compared to 1C8 (p=0.05). FIG. 2B is similar to FIG. 2A except that both groups were larger in size (n=20) and were followed during a longer time period. FIG. 2C shows similar results as FIG. 2A and 2B except that the antibodies were injected repeatedly at days 0, 4 and 10 after surgery.

Figure 3:
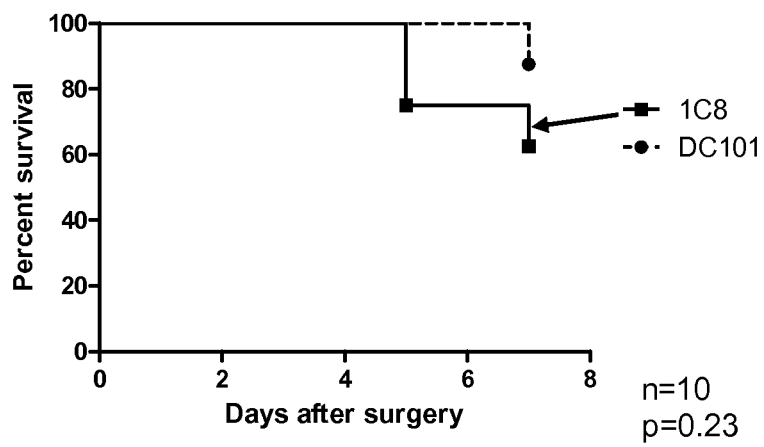
Figure 3:
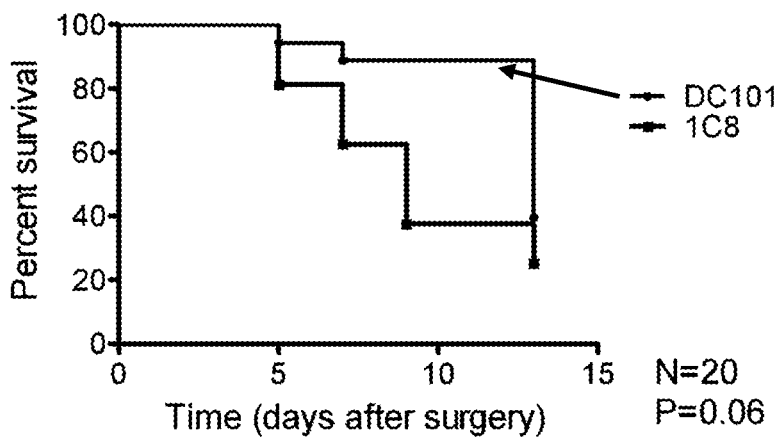
Figure 3:
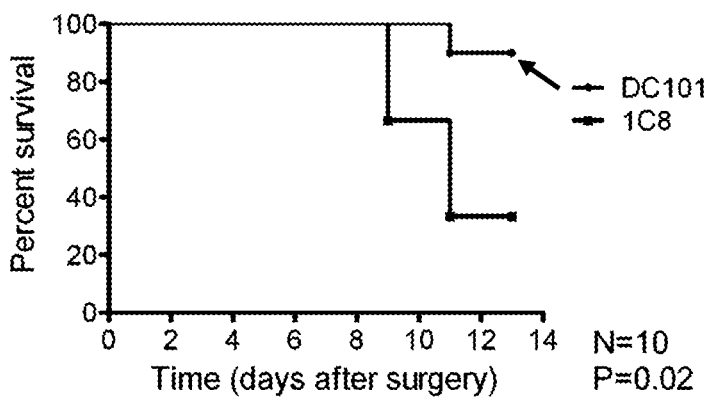

FIG. 3. FIG. 3A shows bleb survival in two groups (group size n=10) that had undergone GFS. One group was treated with 1C8, an irrelevant mouse IgG antibody (4.8 mg/ml) and the other group was treated with DC101, an anti-murine VEGF-R2 antibody (6.2 mg/ml). Bleb survival was not found to be significantly different in the 2 groups (p=0.23). After longer follow-up of two larger groups (n=20; FIG. 3B), significantly increased bleb survival was observed in the DC101-treated group vs the 1C8-treated group (p=0.06). Repeated injection of DC101 (group size n=10) at days 0, 4 and 10 after surgery further increased the bleb survival compared to single injections (FIG. 3C).

Figure 4:
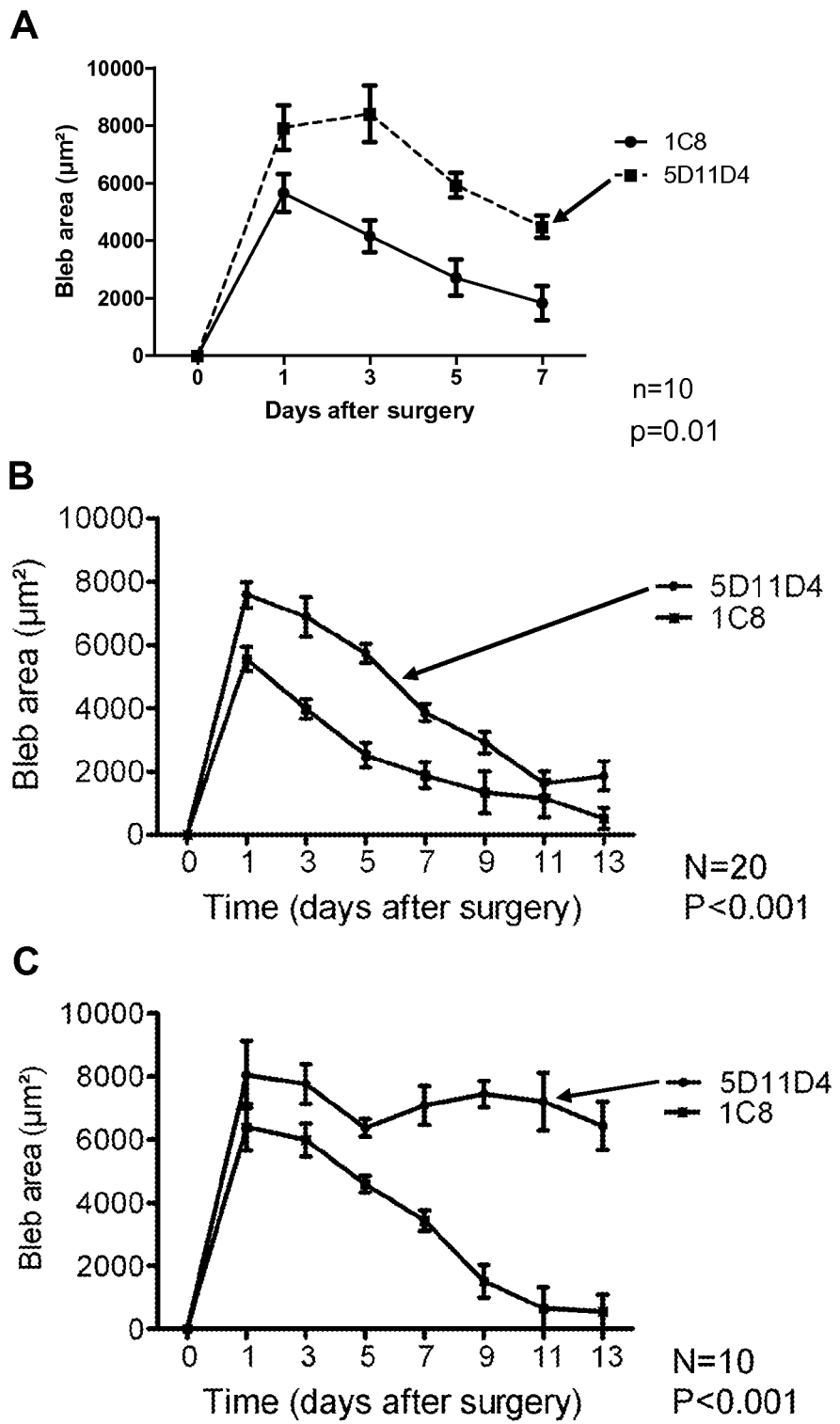

FIG. 4. FIG. 4A shows measurements of bleb area in two groups (group size n=10) that had undergone GFS. One group was treated with 1C8, an irrelevant mouse IgG antibody (4.8 mg/ml) and the other group was treated with 5D11D4, an anti-murine PlGF antibody (5.2 mg/ml). Results are represented as mean±SEM. 5D11D4 significantly improved bleb area as compared to 1C8 (p=0.01). This effect extended till the end of a longer follow-up period of larger groups (n=20; FIG. 4B) and was markedly enhanced by repeat injections of 5D11D4 on days 0, 4 and 10 after surgery (group size n=10; FIG. 4C). The latter effect was significantly more pronounced compared to repeat injections of anti-murine VEGF-R2 antibody DC101 (FIG. 2C/FIG. 6C)

Figure 5:
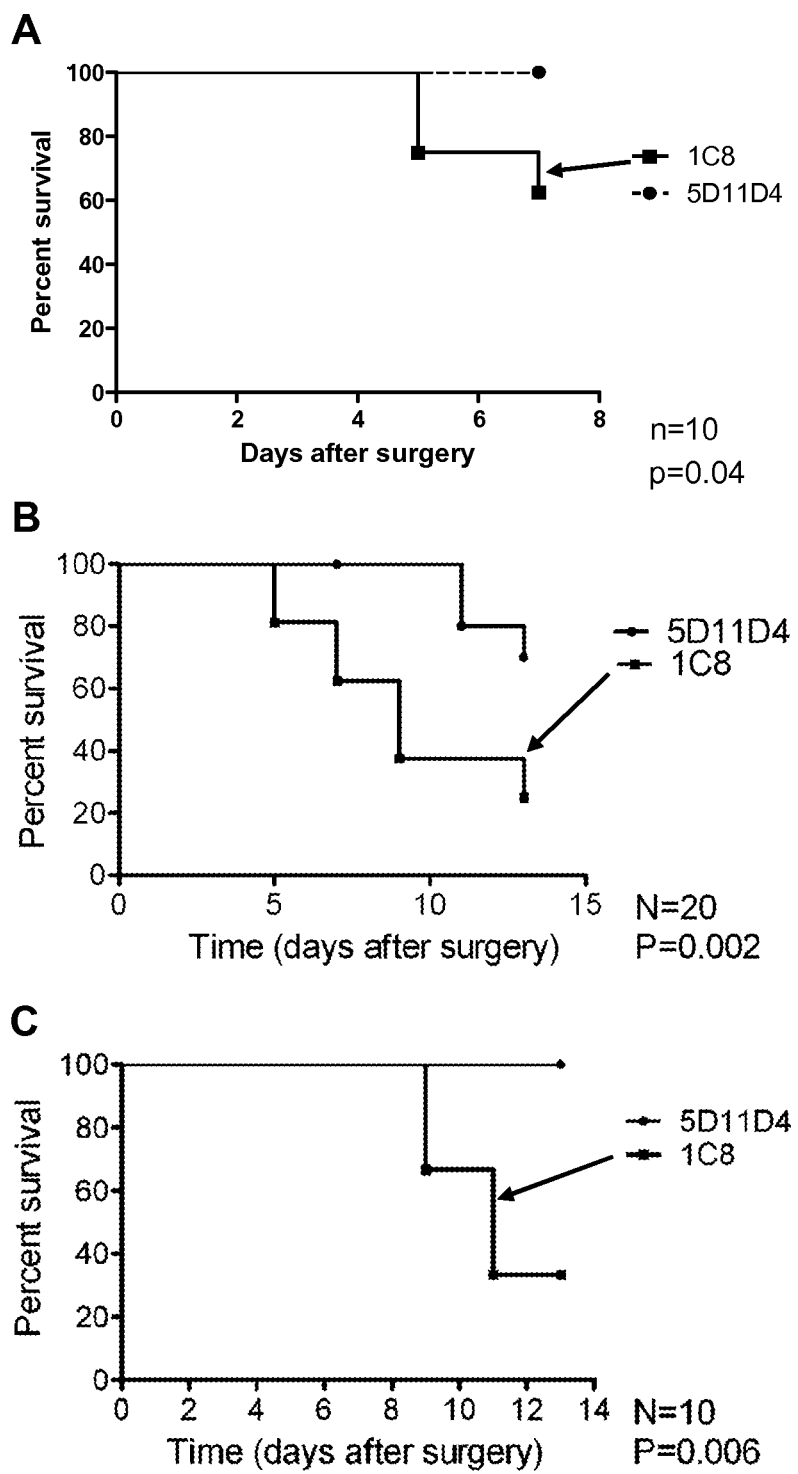

FIG. 5. FIG. 5A shows bleb survival in two groups (group size n=10) that had undergone GFS. One group was treated with 1C8, an irrelevant mouse IgG antibody (4.8 mg/ml) and the other group was treated with 5D11D4, an anti-murine PlGF antibody (5.2 mg/ml). Results are represented as mean±SEM. 5D11D4 significantly improved bleb survival as compared to 1C8 (p=0.04). This effect extended till the end of a longer follow-up period of larger groups (n=20; FIG. 5B) which was significantly more pronounced compared to the anti-murine VEGF-R2 antibody DC101 (FIG. 3B), and was markedly enhanced by repeat injections of 5D11D4 on days 0, 4 and 10 after surgery (group size n=10; FIG. 5C).

Figure 6:
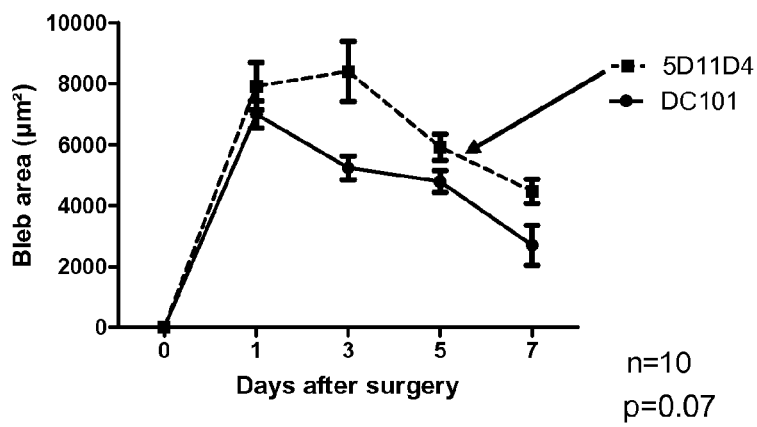
Figure 6:
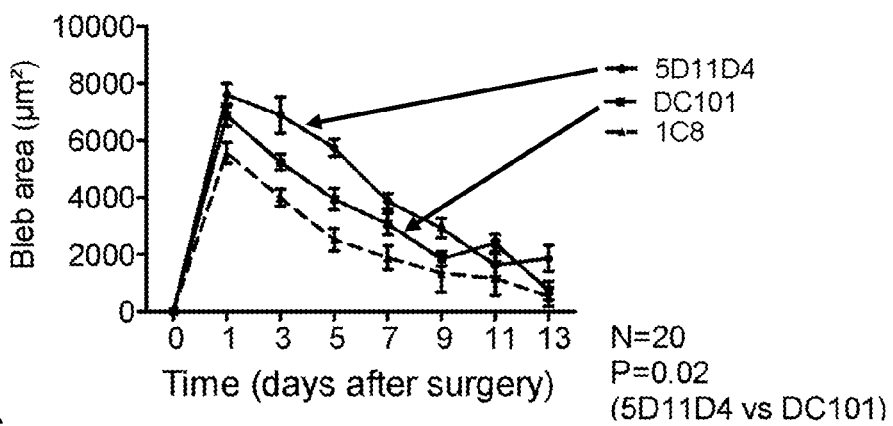
Figure 6:
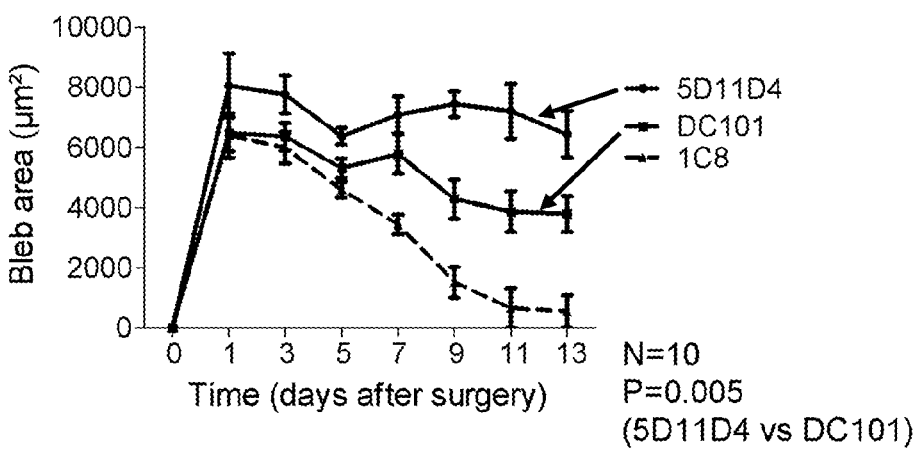

FIG. 6. FIG. 6A shows measurements of bleb area in two groups (group size n=10) that had undergone GFS. One group was treated with DC101, an anti-murine VEGF-R2 antibody (6.2 mg/ml) and the other group was treated with 5D11D4, an anti-murine PlGF antibody (5.2 mg/ml). Results are represented as mean±SEM. 5D11D4 significantly improved bleb area as compared to 1C8 (FIG. 1). A trend towards an increased bleb area after 5D11D4 administration was observed compared to DC101 delivery (p=0.07). The latter was confirmed and strengthened when observing two groups (group size n=20) for a longer time period (FIG. 6B). The stronger effect of 5D11D4 administration over DC101 administration was moreover clearly obviated when comparing the effect of multiple administrations (at days 0, 4 and 10 after surgery; group size n=10) of the antibodies as depicted in FIG. 6C.

Figure 7:
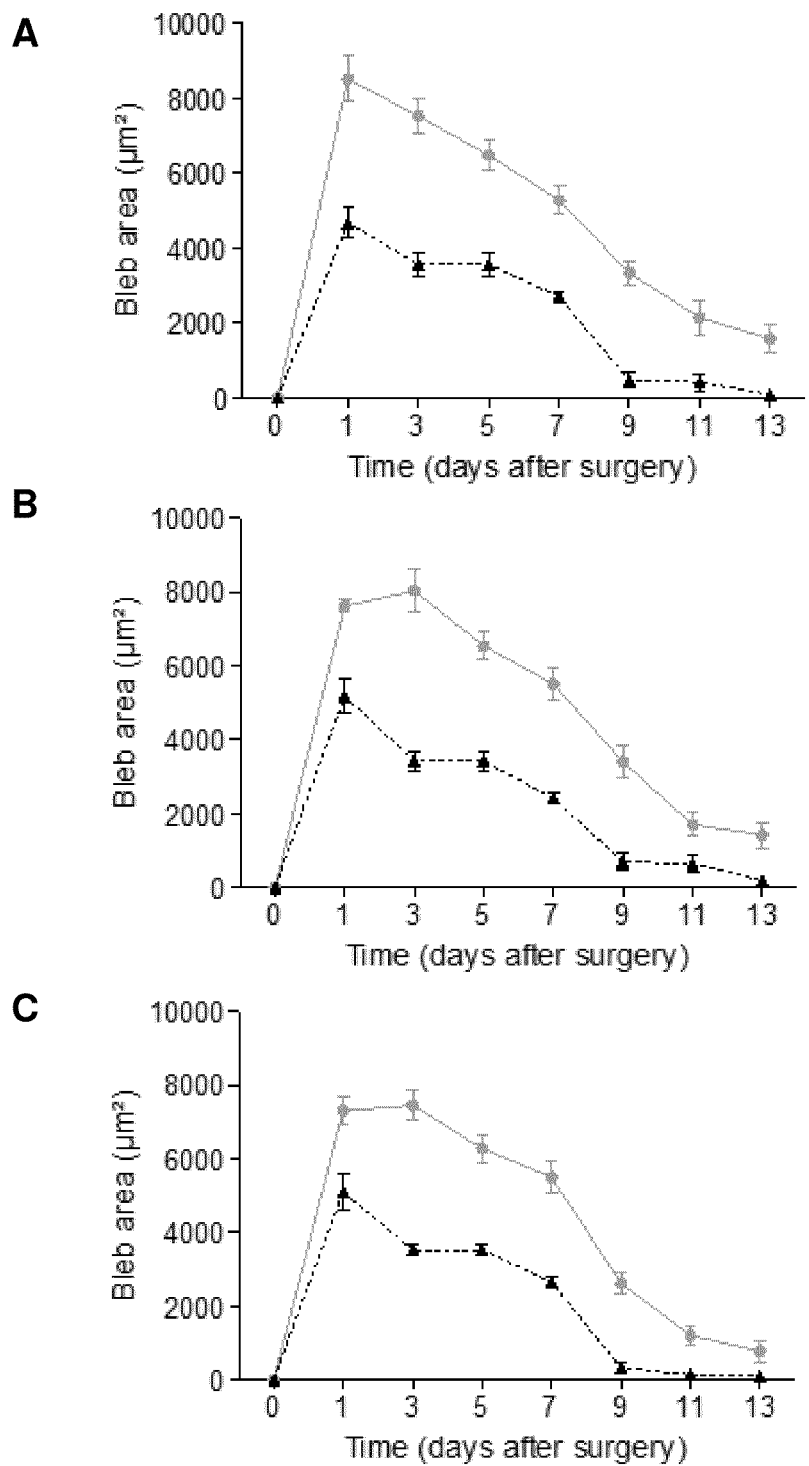

FIG. 7. This figure shows measurement of bleb areas in two groups of mice (group size n=10) that had undergone GFS. One group was treated with 1C8 (filled triangles), an irrelevant mouse IgG antibody (4.8 mg/ml) and the other group was treated with 5D11D4 (filled circles), an anti-murine PlGF antibody (5.2 mg/ml). Results are represented as mean±SEM. FIG. 7A displays the results obtained with injection of the antibodies in the eye's anterior chamber; FIG. 7B displays the results obtained with subconjunctival injection of the antibodies; FIG. 7C displays the results obtained with intravitreal injection of the antibodies. 5D11D4 significantly improved bleb area as compared to 1C8 (p<0.001).

Figure 8:
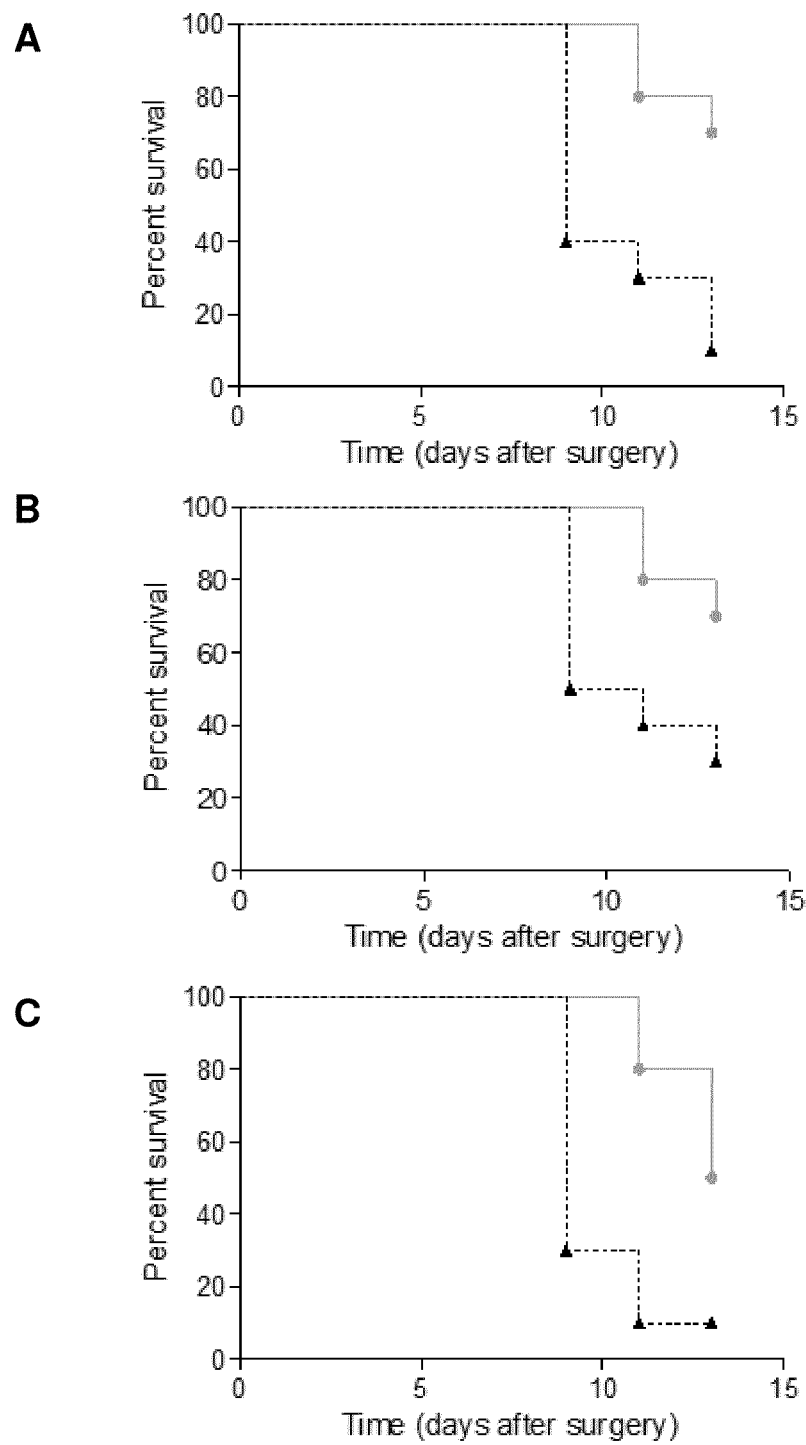

FIG. 8. This figure shows measurement of bleb survival in two groups of mice (group size n=10) that had undergone GFS. One group was treated with 1C8 (filled triangles), an irrelevant mouse IgG antibody (4.8 mg/ml) and the other group was treated with 5D11D4 (filled circles), an anti-murine PlGF antibody (5.2 mg/ml). FIG. 8A displays the results obtained with injection of the antibodies in the eye's anterior chamber; FIG. 8B displays the results obtained with subconjunctival injection of the antibodies; FIG. 8C displays the results obtained with intravitreal injection of the antibodies. 5D11D4 significantly improved bleb survival as compared to 1C8 ($p<0.05$).

Figure 9:
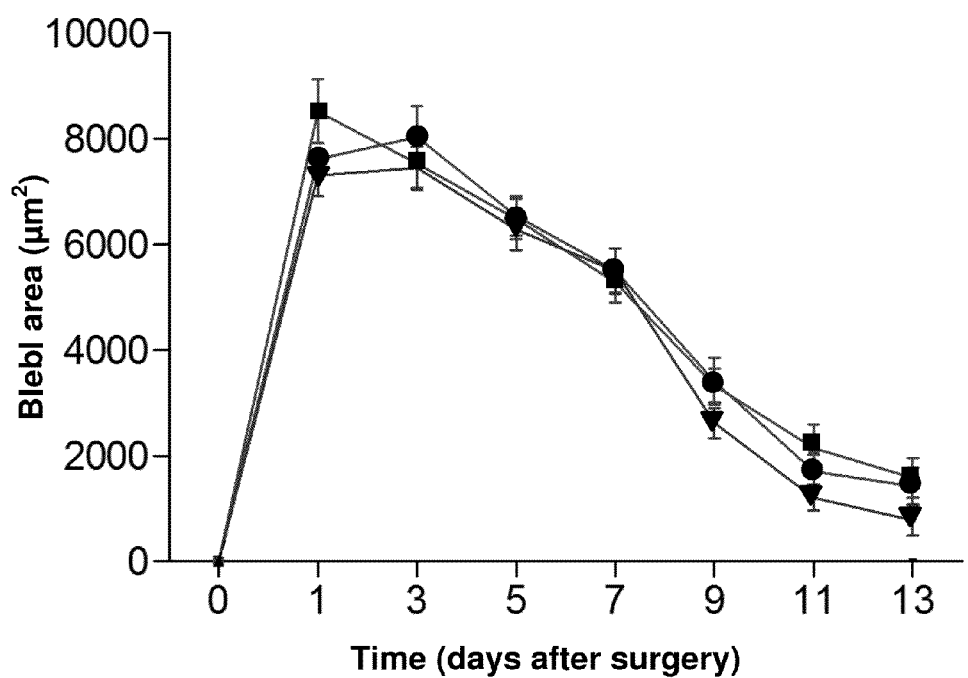

FIG. 9. This figure shows measurement of bleb areas in three groups of mice (group size n=10) that had undergone GFS and that were treated with 5D11D4, an anti-murine PlGF antibody (5.2 mg/ml). Results are represented as mean±SEM. Displayed are the results obtained with injection of the antibodies in the eye's anterior chamber (filled squares), the results obtained with subconjunctval injection of the antibodies (filled circles), and the results obtained with intravitreal injection of the antibodies (filled triangles). No significant difference was detected between the effects on bleb area exerted by the anti-PlGF antibodies administered via the three different routes.

DETAILED DESCRIPTION OF THE INVENTION

As known from clinical practice, each subject or patient undergoing trabeculectomy surgery is at significant risk to develop filtration failure. The present invention is based on the effect of administration of an anti-PlGF antibody (in particular an antibody inhibiting an or the activity of placental growth factor, PlGF) on the clinical outcome of trabeculectomy surgery, said effect being positive and resulting in the prevention, reduction or retardation of the occurrence of filtration failure. The effects obtained with an anti-PlGF antibody are moreover markedly and unexpectedly more pronounced than the effects obtained with an inhibitor of VEGF-R2 (vascular endothelial growth factor receptor 2, known to bind VEGF) or obtained with inhibitors of $VEGF_{165}$ (pegaptanib; Van Bergen et al. 2011, Exp Eye Res 93, 689-699) or of VEGF (bevacizumab; Li et al. 2009, Invest Ophthalmol Vis Sci 50, 5217-5225).

Therefore, the invention relates to an anti-PlGF antibody or fragment thereof for treating filtration failure after trabeculectomy surgery of an eye, or for improving the success rate of trabeculectomy surgery, or for increasing or enhancing the success rate of trabeculectomy surgery, or for preventing, reducing or retarding the occurrence of filtration failure after trabeculectomy surgery of an eye; all evidently as compared to trabeculectomy surgery performed without using an anti-PlGF antibody or fragment thereof. Alternatively, the invention relates to the use of anti-PlGF antibody or fragment thereof for the manufacture of a medicament for, or in a method of, treating filtration failure after trabeculectomy surgery of an eye, or for/of improving the success rate of trabeculectomy surgery, or for/of increasing or enhancing the success rate of trabeculectomy surgery, or for/of preventing, reducing or retarding the occurrence of filtration failure after trabeculectomy surgery of an eye; all evidently as compared to trabeculectomy surgery performed without using an anti-PlGF antibody or fragment thereof. The terms "glaucoma filtration surgery", "filtration surgery" and "trabeculectomy surgery" are used herein interchangeably.

The "trabecular meshwork (TM)" is a mesh-like structure inside the eye at the iris-scleral junction of the anterior chamber angle. The TM filters the aqueous fluid and controls its flow into the canal of Schlemm prior to its leaving the anterior chamber. Increased resistance in the TM leads to reduced aqueous fluid outflow and thus increased intra-ocular pressure (IOP). When left untreated, this elevated IOP leads to glaucomatous damage to the optic nerve and retinal nerve fibers, and leads to loss of vision. This vision loss can be prevented or halted by administering medication, an "agent for controlling the intra-ocular pressure", which controls the intra-ocular pressure. Such medicaments include adrenergic blocking agents (beta blockers or sympatholytic drugs such as betaxolol, carteolol, levobunolol, metipanolol and timolol), adrenergic stimulating agents (sympathomimetic drugs such as aproclonidine, epinephrine, hydroxyamphetamine, phenylephrine, naphazoline and tetrahydrozaline), carbonic anhydrase inhibitors (such as systemic acetozolamide, and topical brinzolamide and dorzolamide), miotics (cholinergic stimulating agents, parasympathomimetic drugs such as carbachol and pilocarpine), osmotic agents (such as glycerin and mannitol), prostaglandin and prostaglandin analogues (prostamides, bimatoprost, unoprostone isopropyl, travoprost, latanoprost, natural prostaglandin, prostaglandin $F2\alpha$, and FP prostanoid receptor agonists). When such medicaments are not efficient (or not anymore), then filtration surgery is a viable treatment.

"Trabeculectomy", "trabeculectomy surgery" or "filtration surgery", or "glaucoma filtration surgery", is defined as a surgical procedure on the eye wherein part of the trabecular meshwork is removed whereby a filtration site (a sclera-corneal drainage channel) is created that increases the outflow of aqueous fluid from the eye; this type of filtering procedure is commonly used in the treatment of glaucoma, and more specifically to reduce the IOP in an eye subject to/suffering from glaucoma.

"Filtration failure" is a condition reversing the clinically desired effect of trabeculectomy surgery, i.e., reversing the desired drop in IOP. The initial post-operative time is crucial in the sense that eye-healing activities are highest in this period. This period of high eye-healing capacity is dependent upon the species and spans about 2 weeks for rabbits and up to 1- to 2-months in humans. Upon contacting an anti-PlGF antibody or fragment thereof with an eye according to the current invention, the frequency of occurrence of filtration failure over a given period of time is lowered. The anti-PlGF antibody or fragment thereof used according to the current invention thus results in the prevention, reduction or retarding of the occurrence of filtration failure, or in an improvement, enhancement or increase of the success rate of trabeculectomy surgery (compared to trabeculectomy surgery without administering or using an anti-PlGF antibody or fragment thereof).

The anti-PlGF antibody or fragment thereof, or a medicament comprising it, may be in a pharmaceutically acceptable formulation (or composition or solution) capable of being administered to an eye. In particular, said formulation (or composition or solution) is capable of being administered into the anterior chamber of the eye or compatible with administration into the anterior chamber of the eye. Alternatively, said formulation (or composition or solution) is capable of being administered into the vitreous (i.e. intravitreal administration) or compatible with administration into the vitreous. In another alternative, said formulation (or composition or solution) is capable of being administered into the subconjunctiva (i.e. subconjunctival administration) or compatible with administration into the subconjunctiva. Further alternatively, said formulation (or composition or solution) is capable of being administered into the surgically created bleb (i.e., in-bleb administration) or compatible with administration into such bleb. The anti-PlGF antibody or fragment thereof, or a medicament comprising it, may be in a pharmaceutically acceptable formulation (or composition or solution) capable of being administered to an eye in the form eye drops. Said administration may e.g. be by injection of the formulation (or composition or solution) or medicament comprising an anti-PlGF antibody or fragment thereof, such as in the case of administration into the anterior chamber, into the vitreous, into the subconjunctiva or into the bleb. Alternatively, said administration may occur in the form of eye drops. Although not required, there may be an additional advantage in said formulation being a slow-release formulation such as a gel-like formulation.

The improvement, enhancement or increase of the success rate of trabeculectomy surgery (or glaucoma filtration surgery) of an eye, or of the prevention, reduction or retardation of the occurrence of filtration failure after trabeculectomy surgery of an eye may result from introduction into the eye of an effective amount of at least a single dose of an anti-PlGF antibody (or fragment thereof) or of a formulation (or composition or solution) or medicament comprising it. In particular, the location of said administration is into the anterior chamber of an eye, into the vitreous of an eye, into the subconjunctiva of an eye, or into the bleb created by glaucoma filtration surgery of an eye, or is a combination thereof. Alternatively, said administration is occurring in the form of (administering an effective dose of) eye drops containing an anti-PlGF antibody or fragment thereof, possible combined with administration via another route (e.g. with one or more of administration in the anterior chamber, intravitreal administration, subconjunctival administration, in-bleb administration). Multiple doses of an effective amount of said anti-PlGF antibody or fragment thereof (or of a formulation (or composition or solution) or medicament comprising it) may be administered, such as to increase efficacy. When multiple doses are administered to an eye, these may be administered with at least 6-hour time intervals, with about 12-hour time intervals, with about 18-hr time intervals, with about 1-day time intervals, with about 2-day time intervals, with about 3-day time intervals, with about 4-day time intervals, with about 7-day time intervals, with about 2-week time intervals with about 1-month time intervals, with about 2-month time intervals or with about 3-month time intervals. When multiple doses are administered to an eye with time intervals, the time interval between two subsequent doses may change during the treatment depending on the evolution of the clinical result. For example, time intervals between subsequent doses may be short immediately after the trabeculectomy surgery and may increase with increasing time after the trabeculectomy surgery. In case of administration of multiple doses, each individual dose may be administered into the anterior chamber of said eye, may be administered into the vitreous of said eye, may be administered in the subconjunctiva of said eye, may be administered into the bleb created by the trabeculectomy surgery of said eye, or may be administered as eye drops to said eye. Said multiple doses, when separated in time, thus could all individually be applied in the same location (e.g. anterior chamber or vitreous) or could all individually be applied in a different location, or could partially be applied in the same location and partially in (oner or more) different locations. Any order of administration in different locations is possible. If for example two administrations are envisaged, then a first administration could be intravitreal (or another location) and the second in the anterior chamber (or another location different from the location of first administration), or vice versa. Alternatively, said multiple doses could all or in part be administered at once via different contacting routes such as for example combined concurrent administration in the anterior chamber and via eye drops.

In any of the above, said anti-PlGF antibody may be any type of antibody or any fragment of any thereof that is capable of binding to PlGF and of inhibiting an activity of PlGF. In particular, said anti-PlGF antibody or fragment thereof may be neutralizing an activity of PlGF, thus may be a neutralizing anti-PlGF antibody or neutralizing anti-PlGF antibody fragment. Such antibodies include all types of antibodies known in the art, such as human or humanized antibodies, cameloid antibodies, nanobodies, domain antibodies, mono- or plural-specific antibodies, etc., and any fragment of any thereof. Examples of anti-PlGF antibodies are described in WO 01/85796 and WO 2006/099698. In particular, an anti-PlGF antibody for use as described herein is effective in inhibiting the activity of placental growth factor as present in the subject undergoing trabeculectomy. In particular, said subject is a mammal, more in particular a human.

The invention further covers an anti-PlGF antibody (or any fragment thereof) as described above for improving, enhancing or increasing the success rate of trabeculectomy surgery, or for treating filtration failure after trabeculectomy surgery of an eye, or for preventing, reducing or retarding the occurrence of filtration failure after trabeculectomy surgery of an eye, wherein the anti-PlGF antibody or fragment thereof is in a pharmaceutically acceptable formulation (or composition or solution) that may further comprise one or more of an agent for controlling the intra-ocular pressure, an anti-inflammatory agent, an antiviral agent, an antibacterial agent, an antiviral agent, an anti-angiogenic agent, an anti-mitotic agent, an antihistamine, an anesthetic, an agent to induce mydriasis and an agent to induce cycloplegia. Alternatively, when said further agent is, or said further agents are, not included in the pharmaceutically acceptable formulation (or composition or solution) containing said anti-PlGF antibody (or any fragment thereof), said eye may be contacted further with one or more agents chosen from an agent for controlling the intra-ocular pressure, an anti-inflammatory agent, an antiviral agent, an antibacterial agent, an antiviral agent, an anti-angiogenic agent, an anti-mitotic agent, an antihistamine, an anesthetic, an agent to induce mydriasis and an agent to induce cycloplegia. Such further contacting may be prior to, concurrent with, or after the administration of an anti-PlGF antibody or any fragment thereof (or of a formulation, composition, solution, or medicament comprising it).

The invention further covers the use of an anti-PlGF antibody (or any fragment thereof) as described above for the manufacture of a medicament for improving, enhancing or increasing the success rate of trabeculectomy surgery, or for treating filtration failure after trabeculectomy surgery of an eye, or for preventing, reducing or retarding the occurrence of filtration failure after trabeculectomy surgery of an eye, wherein the anti-PlGF antibody or fragment thereof is in a pharmaceutically acceptable composition that may further comprise one or more of an agent for controlling the intra-ocular pressure, an anti-inflammatory agent, an antiviral agent, an antibacterial agent, an antiviral agent, an anti-angiogenic agent, an anti-mitotic agent, an antihistamine, an anesthetic, an agent to induce mydriasis and an agent to induce cycloplegia. Alternatively, when said further agent is, or said further agents are, not included in the pharmaceutically acceptable formulation (or composition or solution) or medicament containing said an anti-PlGF antibody (or any fragment thereof), said eye may be contacted further with one or more agents chosen from an agent for controlling the intra-ocular pressure, an anti-inflammatory agent, an antiviral agent, an antibacterial agent, an antiviral agent, an anti-angiogenic agent, an anti-mitotic agent, an antihistamine, an anesthetic, an agent to induce mydriasis and an agent to induce cycloplegia. Such further contacting may be prior to, concurrent with, or after the administration of an anti-PlGF antibody or any fragment thereof (or of a formulation, composition, solution, or medicament comprising it).

Methods of improving, increasing or enhancing the success rate of trabeculectomy surgery of an eye, of treatment of filtration failure after trabeculectomy surgery of an eye, and methods of preventing, reducing or retarding the occurrence of filtration failure after trabeculectomy surgery of an eye are also envisaged. These methods comprise the step of contacting said eye after trabeculectomy surgery with an effective amount of an anti-PlGF antibody (or a fragment thereof) wherein said contacting results in said improvement, increase or enhancement of the success rate of trabeculectomy surgery treatment of an eye, in said treatment of filtration failure after trabeculectomy surgery of an eye, or in said preventing, reducing or retarding of the occurrence of filtration failure after trabeculectomy surgery of an eye. In such methods, the eye may further be contacted with an agent for controlling the intra-ocular pressure, an anti-inflammatory agent, an antiviral agent, an antibacterial agent, an antiviral agent, an anti-angiogenic agent, an anti-mitotic agent, an antihistamine, an anesthetic, an agent to induce mydriasis and an agent to induce cycloplegia. Such further agent different from an anti-PlGF antibody (or fragment thereof) may be co-administered with the anti-PlGF antibody in the same formulation (or composition or solution) or medicament, or concurrently in a separate formulation (or composition or solution) or medicament. Such further agent different from an anti-PlGF antibody (or fragment thereof) may alternatively be administered prior to or after administration of the anti-PlGF antibody (or fragment thereof).

"Contacting" means any mode of administration that results in interaction between an agent or composition such as a medicament and an object (such as conjunctiva or subconjunctival tissue) with which said agent or composition is contacted. The interaction between the agent or composition and the object can occur starting immediately or nearly immediately with the administration of the agent or composition, can occur over an extended time period (starting immediately or nearly immediately with the administration of the agent or composition), or can be delayed relative to the time of administration of the agent or composition. More specifically the "contacting" results in delivering an effective amount of the agent, composition or medicament to the object.

The term "effective amount" refers to the dosing regimen of the agent, composition or medicament according to the invention, in particular of the active ingredient of the medicament according to the invention, i.e., an anti-PlGF antibody or a fragment thereof. The effective amount will generally depend on and will need adjustment to the mode of contacting or administration. The effective amount of the agent, composition or medicament, more particular its active ingredient, is the amount required to obtain the desired clinical outcome or therapeutic or prophylactic effect without causing significant or unnecessary toxic effects. To obtain or maintain the effective amount, the agent, composition or medicament may be administered as a single dose or in multiple doses. The effective amount may further vary depending on the severity of the condition that needs to be treated or the expected severity of the condition that needs to be prevented or treated; this may depend on the overall health and physical condition of the patient and usually the treating doctor's or physician's assessment will be required to establish what is the effective amount. The effective amount may further be obtained by a combination of different types of contacting or administration. In the context of the present invention the effective amount may more particularly be obtained by either one or more of administration of topical eye drops, administration by injection into the anterior chamber of an eye or administration by subconjunctival injection. A typical dose of a single administration of the agent, composition or medicament of the invention may comprise 10 µg to 20 mg of the active compound, or alternatively may comprise 10 µg/kg body weight to 20 mg/kg body weight of the active compound. Administration of the medicament of the invention by means of injection typically is kept to a minimum, i.e., the frequency of repeat injections is kept to a minimum. As the first weeks or months post-trabeculectomy (species dependent as described higher) are crucial in the sense that eye-healing activities are highest in this period, the duration of treatment with an agent, composition or medicament according to the present invention should be adjusted to this period.

In general, the formulation (or composition or solution) or medicament of the invention comprising an anti-PlGF antibody or fragment thereof according to the invention may, depending on its ultimate use and mode of administration, comprise one or more further active ingredients such as an agent controlling the intra-ocular pressure (see higher), an anticoagulant, a thrombolytic agent, an anti-inflammatory agent, an antiviral agent, an antibacterial agent, an antifungal agent, an anti-angiogenic agent, an anti-mitotic agent, an antihistamine or anesthetic.

"Anticoagulants" include hirudins, heparins, coumarins, low-molecular weight heparin, thrombin inhibitors, platelet inhibitors, platelet aggregation inhibitors, coagulation factor inhibitors, anti-fibrin antibodies and factor VIII-inhibitors (such as those described in WO 01/04269 and WO 2005/016455).

"Thrombolytic agents" include urokinase, streptokinase, tissue-type plasminogen activator (tPA), urokinase-type plasminogen activator (uPA) and staphylokinase or any variant or derivative of any thereof such as APSAC (anisoylated plasminogen streptokinase activator complex), alteplase, reteplase, tenecteplase, and scuPA (single chain uPA), plasmin or any truncated variant thereof such as midiplasmin, miniplasmin, deltaplasmin and microplasmin.

"Anti-inflammatory agents" include steroids (e.g. prednisolone, methylprednisolone, cortisone, hydrocortisone, prednisone, triamcinolone, dexamethasone) and non-steroidal anti-inflammatory agents (NSAIDs; e.g. acetaminophren, ibuprofen, aspirin).

"Antiviral agents" include trifluridine, vidarabine, acyclovir, valacyclovir, famciclovir, and doxuridine.

"Antibacterial agents" or antibiotics include ampicillin, penicillin, tetracycline, oxytetracycline, framycetin, gatifloxacin, gentamicin, tobramycin, bacitracin, neomycin and polymyxin. "Anti-mycotic/fungistatic/antifungal agents" include fluconazole, amphotericin, clotrimazole, econazole, itraconazole, miconazole, 5-fluorocytosine, ketoconazole and natamycin.

"Anti-angiogenic agents" include antibodies (or fragments thereof) such as anti-VEGF (vascular endothelial growth factor) or anti-PlGF (placental growth factor) antibodies and agents such as macugen (pegaptanib sodium), trypthophanyl-tRNA synthetase (TrpRS), anecortave acetate, combrestatin A4 prodrug, AdPEDF (adenovector capable of expressing pigment epithelium-derived factor), VEGF-trap, inhibitor of VEGF receptor-2, inhibitors of VEGF, PlGF or TGF-β, Sirolimus (rapamycin) and endostatin.

"Anti-mitotic agents" include mitomycin C and 5-fluorouracyl.

"Antihistamine" includes ketitofen fumarate and pheniramine maleate.

"Anesthetics" include benzocaine, butamben, dibucaine, lidocaine, oxybuprocaine, pramoxine, proparacaine, proxymetacaine, tetracaine and amethocaine.

Other adjunct agents or drugs that can be used in conjunction with the anti-PlGF antibody or fragment thereof according to the invention include scopoloamine, atropine or tropicamide, to induce mydriasis (pupillary dilation) and/or cycloplegia (paralysis of the eye focusing muscle).

In addition to the anti-PlGF antibody or fragment thereof, each of the above listed agents as well as antihistamine and anesthetics is to be considered as an "active ingredient".

A "pharmaceutically acceptable formulation" is, in the context of the current invention more particular an "ophthalmologically acceptable formulation". A formulation in general is a composition comprising a carrier, diluent or adjunvant compatible with the one or more active ingredients to be formulated, the whole formulation being compatible with the intended use in the intended tissue or organ, etc. Examples of pharmaceutically acceptable formulations as well as methods for making them can be found, e.g., in Remington's Pharmaceutical Sciences (e.g. 20$^{th}$ Edition; Lippincott, Williams & Wilkins, 2000) or in any Pharmacopeia handbook (e.g. US-, European- or International Pharmacopeia).

"Lubricants" include propylene glycerol, glycerin, carboxymethylcellulose, hydroxypropylmethylcellulose, soy lecithin, polyvinyl alcohol, white petrolatum, mineral oil, povidone, carbopol 980, polysorbate 80, dextran 70.

EXAMPLES

The Examples included hereafter demonstrate the invention and are not construed to be limiting the scope of the invention in any way.

Example 1

Anterior Chamber Administration

PURPOSE. Excessive postoperative wound healing with subsequent inflammation and scarring frequently leads to surgical failure of glaucoma filtration surgery (GFS). The hypothesis was checked that placental growth factor (PlGF) plays a role in scar formation after GFS, and that it may be a target for improvement of the outcome of this surgery.

METHODS. Aqueous humor and plasma samples of glaucoma and control patients (n=10) were collected and PlGF levels were determined by ELISA. The effect of the anti-murine PlGF-antibody (5D11D4) was investigated in a mouse model of GFS in C75B1/6 mice. In the single-injection setting, 5D11D4 (1 µl; 5.2 mg/ml; antibody described in detail in WO 01/85796) or 1C8, an irrelevant mouse IgG antibody against human tissue plasminogen activator (1 µl; 4.8 mg/ml; antibody available at ThromboGenics), were injected in the anterior chamber (n=10 eyes or n=20 eyes for both groups) immediately after surgery ("day 0"). An anti-murine VEGF-R2 antibody (DC101) was used as a positive control (1 µl; 6.2 mg/ml; n=10). Mice were killed on postoperative day 8. In the multiple- or repeated-injection setting, the antibodies were administered as above, albeit it on days 0, 4 and 10 after surgery; groups of n=10 eyes were assessed; and mice were killed on post-operative day 13. Treatment outcome was studied by clinical investigation of intra-ocular pressure (IOP), bleb area and bleb survival every other day.

RESULTS. PlGF levels in aqueous humor were found to be significantly upregulated in glaucoma compared to control patients (17±2 pg/ml versus 12±0.75 pg/ml, p=0.03). No significant differences were found in plasma concentrations of PlGF. In the mouse model of GFS, single administration of the anti-PlGF antibody (5D11D4) significantly improved surgical outcome by increasing bleb survival (p=0.04) and bleb area (p=0.01) with 29% compared to negative control (1C8). A single administration of anti-VEGF-R2 (DC101) also significantly improved bleb area with 7% as compared to 1C8 (p=0.05), but had no effect on bleb survival (p=0.23). A trend towards an increased bleb area after 5D11D4 administration was observed compared to DC101 delivery (p=0.07). IOP was not found to be significantly different in any of the groups (p>0.05). Results of single administration of the antibodies are depicted in FIG. 1 (IOP); FIGS. 2A, 2B, 4A, 4B, 6A and 6B (all bleb area); and FIGS. 3A, 3B, 5A and 5B (bleb survival).

Multiple- or repeated administrations of the antibodies (at days 0, 4 and 10 after surgery) led to a more pronounced improvement of surgical outcome with both 5D11D4 and DC101 separately compared to 1C8, and with a more pronounced positive outcome with 5D11D4 compared to DC101. Furthermore, the trend towards an increased bleb area after 5D11D4 administration compared to DC101 upon single administration (p=0.07) was converted into a significant difference. The latter further proves that an anti-PlGF antibody (5D11D4) is more efficient in improving surgical outcome of GFS than an anti-VEGF-R2 antibody (DC101) (p=0.005). Results of repeated administrations of the antibodies are depicted in FIGS. 2C, 4C and 6C (all bleb area); and FIGS. 3C and 5C (bleb survival).

CONCLUSIONS. Local production of PlGF in the eye may indicate an important role for this growth factor in wound healing after GFS. Indeed, targeting PlGF with an inhibitory monoclonal antibody is efficacious in improving GFS outcome, even more efficacious than inhibition of VEGF-R2 as described herein, and more efficacious than inhibition of VEGF-165 (Van Bergen et al. 2011, Exp Eye Res 93, 689-699) or VEGF-A (Li et al. 2009, Invest Ophthalmol Vis Sci 50, 5217-5225). This effect is seen with single administration of an anti-PlGF antibody and is significantly enhanced upon multiple administrations of an anti-PlGF antibody. These results render PlGF a validated target for ocular wound healing and point to the therapeutic benefits of PlGF-inhibition in this setting.

Example 2

Comparison of Anterior Chamber Administration, Intravitreal Administration and Subconjunctival Administration Mouse Model of Glaucoma Filtration Surgery C57BL/6J mice (8-10 weeks old, Charles River Laboratories) were used in accordance with the standards in the Association for Research in Vision and Ophthalmology Statement for the Use of Animals in Ophthalmic and Vision Research. The Institutional Animal Care and Research Advisory Committee of KU Leuven approved all experimental animal procedures. Mice were anesthetized with an intaperitoneal injection of 10 times-diluted (60 mg/kg final dose) sodium pentobarbital (Nembutal, 60 mg/ml; CEVA, Sante Animale). Filtering surgery was performed on both eyes, using a technique that has been described previously and that results in a filtering bleb. In the first experiment (n=10 eyes for all groups), mice were divided in different groups to investigate different administration route of the PlGF-antibody. Immediately after surgery, the PlGF inhibitor (5.2 µg) was intracamerally (anterior chamber) injected in the first group of mice, subconjunctivally in the second group and the third group received an intravitreal injection of 5D11D4. The isotype matched control antibody (1C8) was used in every group as a negative control. The injections were performed by using an analytic science syringe (SGE Analytic Science) and glass capillaries with a diameter of 50-70 µm at the end, controlled by the UMP3I Microsyringe Injector and Micro4 Controller (all from World Precision Instruments, Inc).

Mice were clinically examined on day 1 after surgery and then every 2 days until they were sacrificed. The bleb area (width and length) were analyzed under topical anesthesia. Commercial software (KS300; Zeiss) was used to determine the bleb size on bleb images of mice. These pictures were taken using a digital camera (Canon PowerShot S50) using a 3× optical zoom lens at a magnification of 4×. Bleb survival was taken as the end-point of the study, while bleb failure was defined as the appearance of a scarred and flat bleb at 2 consecutive measurements.

Statistical Analysis

Data at individual time points were analyzed using mixed model analysis for repeated measures (using GraphPad Prism 5). Kaplan-Meier survival analysis was performed for bleb failure using the logrank test. $P<0.05$ was considered to be statistically significant. Data are represented as mean±SEM.

Results

Optimal Route of Administration of the Anti-PlGF Antibody

Previous study showed intra-ocular safety of anti-PlGF injections in the eye, however, the most optimal route of administration of the PlGF-antibody is still uncertain. Therefore, surgical outcome after a single intracameral, subconjunctival and intravitreal injection of the PlGF antibody (5D11D4, 5.2 µg) were compared. Bleb area and bleb survival were analyzed until 14 days after surgery and showed that the three administration routes of the PlGF-antibody were able to significantly improve bleb area (n=10; $P<0.001$) and bleb survival (n=10; $P<0.05$) compared to their respective controls (1C8; 4.8 µg) (FIGS. 7 and 8). A direct comparison between the three groups showed no significant difference neither in bleb area (FIG. 9), nor in bleb survival (n=10; P=NS), indicating that all routes of injection or all routes/locations of administration are equally able to improve surgical outcome.

The invention claimed is:

1. A method of enhancing the success rate of trabeculectomy surgery of an eye, of treating filtration failure after trabeculectomy surgery of an eye, or of reducing or retarding the occurrence of filtration failure after trabeculectomy surgery of an eye, said method comprising the step of administering an anti-placental growth factor (PlGF) antibody or PlGF-binding fragment thereof to said eye, thereby enhancing the success rate of trabeculectomy surgery of an eye, treating filtration failure after trabeculectomy surgery of an eye, or reducing or retarding the occurrence of filtration failure after trabeculectomy surgery, wherein said anti-PlGF antibody or PlGF-binding fragment thereof binds to PlGF and inhibits PlGF.

2. The method according to claim 1 wherein at least a single dose of an effective amount said anti-PlGF antibody or PlGF-binding fragment thereof is administered to said eye.

3. The method according to claim 1 further comprising administration of one or more agents selected from the group consisting of an agent for controlling intra-ocular pressure, an anti-inflammatory agent, an antiviral agent, an antibacterial agent, an anti-angiogenic agent, an anti-mitotic agent, an antihistamine, an anesthetic, an agent to induce mydriasis, and an agent to induce cycloplegia.

4. The method according to claim 3 wherein said further administration occurs prior to, concurrent with, or after administering the anti-PlGF antibody or PlGF-binding fragment thereof.

5. The method according to claim 1 wherein multiple doses of an effective amount of said anti-PlGF antibody or PlGF-binding fragment thereof are administered to said eye.

6. The method according to claim 5 wherein said multiple doses are administered with at least 6-hour time intervals.

7. The method according to claim 5 wherein each of said multiple doses are administered into the anterior chamber of said eye, are administered into the vitreous of said eye, are administered in the subconjunctiva of said eye, are administered into the bleb created by the trabeculectomy surgery of said eye, or are administered as eye drops to said eye.

8. The method according to claim 1 wherein said anti-PlGF antibody or PlGF-binding fragment thereof is administered into the anterior chamber of said eye, is administered into the vitreous of said eye, is administered in the subconjunctiva of said eye, is administered into the bleb created by the trabeculectomy surgery of said eye, or is administered as eye drops to said eye.

9. The method according to claim 1 wherein said anti-PlGF antibody or PlGF-binding fragment thereof is in a pharmaceutically acceptable formulation capable of being administered to an eye.

10. The method according to claim 1 wherein said anti-PlGF antibody or PlGF-binding fragment thereof is in a pharmaceutically acceptable formulation capable of being administered into the anterior chamber of an eye.

11. The method according to claim 1 wherein said anti-PlGF antibody or PlGF-binding fragment thereof is in a pharmaceutically acceptable formulation capable of being administered into the vitreous of an eye.

12. The method according to claim 1 wherein said anti-PlGF antibody or PlGF-binding fragment thereof is in a pharmaceutically acceptable formulation capable of being administered into the subconjunctiva of an eye.

13. The method according to claim 1 wherein said anti-PlGF antibody or PlGF-binding fragment thereof is in a pharmaceutically acceptable formulation capable of being administered into the bleb created by trabeculectomy surgery.

14. The method according to claim 1 wherein said anti-PlGF antibody or PlGF-binding fragment thereof is in a pharmaceutically acceptable eye drop formulation capable of being administered to an eye.

15. The method according to claim 1 wherein said anti-PlGF antibody or PlGF-binding fragment thereof is in a pharmaceutically acceptable formulation further comprising one or more agents selected from the group consisting of an agent for controlling intra-ocular pressure, an anti-inflammatory agent, an antiviral agent, an antibacterial agent, an anti-angiogenic agent, an anti-mitotic agent, an antihistamine, an anesthetic, an agent to induce mydriasis, and an agent to induce cycloplegia.

16. The method of claim 1, wherein the method is for enhancing the success rate of trabeculectomy surgery of an eye.

17. The method of claim 1, wherein the method is for treating filtration failure after trabeculectomy surgery of an eye.

18. The method of claim 1, wherein the method is for reducing or retarding the occurrence of filtration failure after trabeculectomy surgery of an eye.

19. The method of claim 1, wherein the eye is of a human subject.

* * * * *